US006528515B1

(12) United States Patent
Furman et al.

(10) Patent No.: US 6,528,515 B1
(45) Date of Patent: Mar. 4, 2003

(54) COMBINATION THERAPY TO TREAT HEPATITIS B VIRUS

(75) Inventors: Phillip A. Furman, Durham, NC (US); George R. Painter, III, Chapel Hill, NC (US); David W. Barry, Chapel Hill, NC (US); Franck Rousseau, Durham, NC (US)

(73) Assignee: Triangle Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 09/432,247

(22) Filed: Nov. 2, 1999

Related U.S. Application Data
(60) Provisional application No. 60/106,664, filed on Nov. 2, 1998.

(51) Int. Cl.[7] .................. A61K 31/505; A61K 32/52
(52) U.S. Cl. .................. 514/274; 514/264; 514/263; 514/262; 514/261
(58) Field of Search ................. 514/274, 261, 514/262, 263, 264

(56) References Cited

U.S. PATENT DOCUMENTS

| | | |
|---|---|---|
| 4,522,811 A | 6/1985 | Eppstein et al. |
| 5,075,445 A | 12/1991 | Jarvest et al. |
| 5,142,051 A | 8/1992 | Holy et al. |
| 5,149,794 A | 9/1992 | Yatvin et al. |
| 5,179,104 A | 1/1993 | Chu et al. |
| 5,194,654 A | 3/1993 | Hostetler et al. |
| 5,204,466 A | 4/1993 | Liotta et al. |
| 5,223,263 A | 6/1993 | Hostetler et al. |
| 5,234,913 A | 8/1993 | Furman, Jr. et al. |
| 5,256,641 A | 10/1993 | Yatvin et al. |
| 5,411,947 A | 5/1995 | Hostetler et al. |
| 5,444,063 A | 8/1995 | Schinazi |
| 5,463,092 A | 10/1995 | Hostetler et al. |
| 5,486,520 A | 1/1996 | Belleau |
| 5,538,975 A | 7/1996 | Dionne |
| 5,539,116 A | 7/1996 | Liotta et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,565,438 A | 10/1996 | Chu et al. |
| 5,567,688 A | 10/1996 | Chu et al. |
| 5,587,362 A | 12/1996 | Chu et al. |
| 5,618,820 A | 4/1997 | Dionne |
| 5,641,763 A | 6/1997 | Holy et al. |
| 5,674,849 A | 10/1997 | Twist et al. |
| 5,684,010 A | 11/1997 | Schinazi |
| 5,684,153 A | 11/1997 | Geen et al. |
| 5,700,937 A | 12/1997 | Liotta et al. |
| 5,728,575 A | 3/1998 | Liotta et al. |
| 5,756,478 A | 5/1998 | Cheng et al. |
| 5,767,122 A | 6/1998 | Chu et al. |
| 5,808,040 A | 9/1998 | Chu et al. |
| 5,814,639 A | 9/1998 | Liotta et al. |
| 5,827,727 A | 10/1998 | Liotta et al. |
| 5,869,461 A | 2/1999 | Cheng et al. |
| 5,914,331 A | 6/1999 | Liotta et al. |
| 6,071,922 A * | 6/2000 | Schinazi et al. ............ 514/274 |
| 6,177,435 B1 | 1/2001 | Larder et al. |

FOREIGN PATENT DOCUMENTS

| | | |
|---|---|---|
| EP | 0 141 927 | 5/1985 |
| EP | 0 253 412 | 1/1988 |
| EP | 0 494 119 A1 | 3/1992 |
| EP | 0 494 119 | 7/1992 |
| EP | 0 515 144 A1 | 11/1992 |
| EP | 0 382 526 B1 | 5/1996 |
| EP | 0 711 771 A2 | 5/1996 |
| WO | WO 89/02733 | 4/1989 |
| WO | WO 90/00555 | 1/1990 |
| WO | WO 91/16920 | 11/1991 |
| WO | WO 91/17159 | 11/1991 |
| WO | WO 91/18914 | 12/1991 |
| WO | WO 91/19721 | 12/1991 |
| WO | WO 92/18517 | 10/1992 |
| WO | WO 93/00910 | 1/1993 |
| WO | WO 94/09793 | 5/1994 |
| WO | WO 94/26273 | 11/1994 |
| WO | WO 95/20595 | 8/1995 |
| WO | WO 98/23285 | 6/1998 |

OTHER PUBLICATIONS

Medline Abstract, AN 96300556, 1996, Korba et al.*
Medline Abstract, AN 97271965, 1997, Kruger et al.*
Furman, et al., "The Anti–Hepatitis B Virus Activities, Cytotoxicities, and Anabolic Profiles of the (−) and (+) Enantiomers of cis–5–Fluoro–1–[2–(Hydroxymethyl)–1, 3–oxathiolane–5–yl] Cytosine" Antimicrobial Agents and Chemotherapy, Dec. 1992, p. 2686–2692.
Chang, et al., "Deoxycytidine Deaminase–resistant Stereosomer Is the Active Form of (±)–2′, 3′–Dideoxy–3′–thiacytidine in the Inhibition of Hepatitis B Virus Replication", Journal of Biological Chemistry, vol. 267(20), 13938–13942 (1992).
Von Janta–Lipinski et al., "Newly Synthesized L–Enantiomers of 3′Fluoro–Modified B–2′–Deoxyribonucleoside 5′–Triphosphates Inhibit Hepatitis B DNA Polymerases But Not the Five Cellular DNA Polymerases a, B, v, d, and e Nor HIV–1 Reverse Transcriptase", J. Med. Chem., 1998, 41,2040–2046.

(List continued on next page.)

*Primary Examiner*—Russell Travers
*Assistant Examiner*—Shengjun Wang
(74) *Attorney, Agent, or Firm*—Sherry M. Knowles, Esq.; Clark G. Sullivan, Esq.; King & Spalding LLP

(57) ABSTRACT

The present invention is directed to a method for treating hepatitis B virus infection in humans comprising administering a synergistically effective amount of agents having known anti-hepatitis B virus activity in combination or alternation. Specifically, the invention is directed to a method for treating hepatitis B virus infection comprising administering FTC in combination or alternation with penciclovir, famciclovir or Bis-POM-PMEA. Additionally, the invention is directed to a method for treating hepatitis B virus infection comprising administering L-FMAU in combination or alternation with DAPD, penciclovir or Bis-POM-PMEA. The invention is further directed to a method for treating hepatitis B virus infection comprising administering DAPD in combination or alternation with Bis-POM-PMEA.

19 Claims, No Drawings

OTHER PUBLICATIONS

R. Jones and N. Bischofberger, "Minireview: nucleotide prodrugs", Antiviral Research, 27 (1995) 1–17.

Imai, et al., "Studies on Phosphorylation, IV. Selective Phosphorylation of the Primary Hydroxyl Group in Nucleosides", J. Org. Chem., 34(6), 1547–1550 (Jun. 1969).

Davisson, et al., "Synthesis of Nucleotide 5'–Diphosphates from 5'–0–Tosyl Nucleosides", J. Orig. Chem 52(9), 1794–1801 (1987).

Hoard, et al., "Conversion of Mono– and Oligodeoxyribonucleotides to 5'–Triphosphates", J. Am. Chem. Soc., 87(8), 1785–1788 (1965).

Korba and Gerin, "Use of a standardized cell culture assay activities of nucleoside analogs against hepatitis B virus replication", Antiviral Res. 19: 55–70 (1992).

Korba, "In vitro evaluation of combination therapies against hepatitis B virus replication", Antiviral Res. 29: 49–51 (1996).

Migyoung, L "Dioxolane Cytosine Nucleosides as Anti–Hepatitis B Agents" Bioorganic & Medicinal C Chemistry Letters, 5, 17 pp 2011–2014, 1995.

\* cited by examiner

COMBINATION THERAPY TO TREAT HEPATITIS B VIRUS

This application claims priority to U.S. provisional patent application No. 60/106,664, filed on Nov. 2, 1998.

This invention is in the area of methods for the treatment of hepatitis B virus (also referred to as "HBV") that includes administering to a host in need thereof, an effective combination of nucleosides which have known anti-hepatitis B activity.

HBV is second only to tobacco as a cause of human cancer. The mechanism by which HBV induces cancer is unknown, although it is postulated that it may directly trigger tumor development, or indirectly trigger tumor development through chronic inflammation, cirrhosis, and cell regeneration associated with the infection.

Hepatitis B virus has reached epidemic levels worldwide. After a two to three month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is very similar to that of acquired immune deficiency syndrome (AIDS), which accounts for why HBV infection is common among patients with AIDS or AIDS related complex. However, HBV is more contagious than HIV.

However, more recently, vaccines have also been produced through genetic engineering and are currently used widely. Unfortunately, vaccines cannot help those already infected with HBV. Daily treatments with α-interferon, a genetically engineered protein, has also shown promise, but this therapy is only successful in about one third of treated patients. Further, interferon cannot be given orally.

A number of synthetic nucleosides have been identified which exhibit activity against HBV. The (−)-enantiomer of BCH-189, known as 3TC, claimed in U.S. Pat. No. 5,539,116 to Liotta, et al., has been approved by the U.S. Food and Drug Administration for the treatment of hepatitis B. See also EPA 0 494 119 A1 filed by BioChem Pharma, Inc.

β2-Hydroxymethyl-5-(5-fluorocytosin-1-yl)-1,3-oxathiolane ("FTC"), claimed in U.S. Pat. Nos. 5,814,639 and 5,914,331 to Liotta, et al., exhibits activity against HBV. See Furman, et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]Cytosine" *Antimicrobial Agents and Chemotherapy*, December 1992, page 2686–2692; and Cheng, et al., *Journal of Biological Chemistry*, Volume 267(20), 13938–13942 (1992).

U.S. Pat. Nos. 5,565,438, 5,567,688 and 5,587,362 (Chu, et al.) disclose the use of 2'-fluoro-5-methyl-β-L-arabinofuranolyluridine (L-FMAU) for the treatment of hepatitis B and Epstein Barr virus.

U.S. Pat. No. 5,767,122 to Emory University and The University of Georgia Research Foundation, Inc. discloses and claims enantiomerically pure β-D-dioxolanyl nucleosides of the formula:

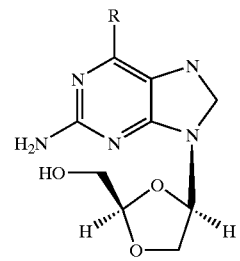

wherein R is $NH_2$, OH, Cl, or H. A method for treating HBV infection using a combination of DAPD and FTC is claimed in U.S. Pat. No. 5,684,010 to Raymond F. Schinazi.

Penciclovir (2-amino-1,9-dihydro-9-[4-hydroxy-3-(hydroxymethyl)butyl]-6H-purin-6-one; PCV) has established activity against hepatitis B. See U.S. Pat. Nos. 5,075,445 and 5,684,153.

Adefovir (9-[2-(phosphonomethoxy)ethyl]adenine, also referred to as PMEA or [[2(6-amino-9H-purin-9-yl)ethoxy] methylphosphonic acid), also has established activity against hepatitis B. See for example U.S. Pat. Nos. 5,641,763 and 5,142,051.

Yale University and The University of Georgia Research Foundation, Inc. disclose the use of L-FDDC (5-fluoro-3'-thia-2',3'-dideoxycytidine) for the treatment of hepatitis B virus in WO 92/18517.

von Janta-Lipinski et al. disclose the use of the L-enantiomers of 3'-fluoro-modified β-2'-deoxyribonucleoside 5'-triphosphates for the inhibition of hepatitis B polymerases (J. Med. Chem., 1998, 41,2040–2046). Specifically, the 5'-triphosphates of 3'-deoxy-3'-fluoro-β-L-thymidine (β-L-FTTP), 2',3'-dideoxy-3'-fluoro-β-L-cytidine (β-L-FdCTP), and 2',3'-dideoxy-3'-fluoro-β-L-5-methylcytidine (β-L-FMethCTP) were disclosed as effective inhibitors of HBV DNA polymerases.

It has been recognized that drug-resistant variants of HBV can emerge after prolonged treatment with an antiviral agent. Drug resistance most typically occurs by mutation of a gene that encodes for an enzyme used in the viral lifecycle, and most typically in the case of HBV, DNA polymerase. Recently, it has been demonstrated that the efficacy of a drug against HBV infection can be augmented by administering the compound in combination with a second, and perhaps third, antiviral compound that induces a different mutation from that caused by the principle drug. Alternatively, the pharmacokinetics, biodistribution, or other parameter of the drug can be altered by such combination therapy. In general, combination therapy induces multiple simultaneous stresses on the virus.

United U.S. Pat. No. 5,808,040 discloses that L-FMAU can be administered in combination with FTC, 3TC, carbovir, acyclovir, interferon, AZT, DDI (2',3'-dideoxyinosine), DDC (2',3'-dideoxycytidine), L-DDC, L-F-DDC, and D4T.

United U.S. Pat. No. 5,674,849 discloses the use of a nucleoside in combination with an oligonucleotide for the treatment of a viral disease.

U.S. Pat. No. 5,684,010 discloses a method for the treatment of hepatitis B that includes administering in combination or alternation a compound of the formula:

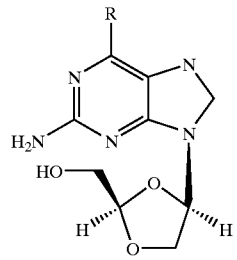

wherein R is $NH_2$, OH, or Cl, with FTC, 3TC, carbovir, or interferon.

WO 98/23285 discloses a method for the treatment or prophylaxis of hepatitis B virus infections in a human or animal patient which comprises administering to the patient effective or prophylactic amounts of penciclovir (or a bioprecursor thereof such as famciclovir) and alpha-interferon.

In light of the fact that hepatitis B virus has reached epidemic levels worldwide, and has severe and often tragic effects on the infected patient, there remains a strong need to provide new effective treatments for humans infected with the virus that have low toxicity to the host.

Therefore, it is an object of the present invention to provide new methods for the treatment of human patients or other hosts infected with hepatitis B virus and related conditions comprising administering a synergistically effective amount of a combination of anti-HBV agents.

SUMMARY OF THE INVENTION

It has been discovered that certain combinations of agents with hepatitis B activity are synergistic, and thus can provide enhanced benefits to the patient when administered in an effective combination or alternation dosage pattern.

In one preferred embodiment of the present invention, a method for treating HBV infection and related conditions in humans is disclosed, comprising administering a synergistically effective amount of β-2-hydroxymethyl-5-(5-fluorocytosin-1-yl)-1,3-oxathiolane (FTC), preferably substantially in the form of the (−)-optical isomer, or a pharmaceutically acceptable salt, ester or prodrug thereof with Penciclovir (2-amino-1,9-dihydro-9-[4-hydroxy-3-(hydroxymethyl)butyl]-6H-purin-6-one, also referred to as "PCV"). Famciclovir, or any other bioprecursor of Penciclovir, can be used in place of Penciclovir in any embodiment of this invention.

Another preferred embodiment of the present invention is a method for treating HBV infection and related conditions in humans, comprising administering in combination or alternation a synergistically effective amount of β-2-hydroxymethyl-5-(5-fluorocytosin-1-yl)-1,3-oxathiolane (FTC), preferably substantially in the form of the (−)-optical isomer, or a pharmaceutically acceptable salt, ester or prodrug thereof, with 9-[2-(phosphonomethoxy)ethyl]adenine (PMEA, also referred to below as Bis-POM-PMEA or BP-PMEA), or a pharmaceutically acceptable salt, ester or prodrug thereof, optionally in a pharmaceutically acceptable carrier.

In another preferred embodiment of the present invention, a method for treating HBV infection and related conditions in humans is disclosed, comprising administering in combination or alternation a synergistically effective amount of 2'-fluoro-5-methyl-β-L-arabinofuranolyluridine (L-FMAU), or a pharmaceutically acceptable salt, ester or prodrug thereof, with a compound of the formula:

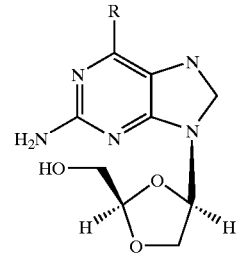

preferably β-D-(2R,4R)-2-amino-9-[(2-hydroxymethyl)-1,3-dioxolan-4-yl]purine (DAPD), which is preferably administered in substantially pure form, or a pharmaceutically acceptable salt, ester or prodrug thereof, optionally in a pharmaceutically acceptable carrier.

In yet another preferred embodiment of the present invention, a method for treating HBV infection and related conditions in humans is disclosed, comprising administering a synergistically effective combination or alternation amount of 2'-fluoro-5-methyl-β-L-arabinofuranolyluridine (L-FMAU), or a pharmaceutically acceptable salt, ester or prodrug thereof, with Penciclovir, or a pharmaceutically acceptable salt, ester or prodrug thereof, optionally in a pharmaceutically acceptable carrier.

In still another preferred embodiment of the present invention, a method for treating HBV infection and related conditions in humans is disclosed, comprising administering a synergistically effective amount of 2'-fluoro-5-methyl-β-L-arabinofuranolyluridine (L-FMAU), or a pharmaceutically acceptable salt, ester or prodrug thereof, with 9-[2-(phosphonomethoxy)ethyl]adenine (PMEA), or a pharmaceutically acceptable salt, ester or prodrug thereof, optionally in a pharmaceutically acceptable carrier.

Another preferred embodiment of the present invention comprises a method for treating HBV infection and related conditions in humans, comprising administering a synergistically effective amount of a compound of the formula:

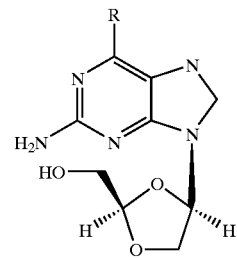

wherein R is $NH_2$, OH, H, or Cl (collectively referred to herein as the DAPD compounds), preferably, β-D-(2R,4R)-2-amino-9-[(2-hydroxymethyl)-1,3-dioxolan-4-yl]purine (DAPD), which is preferably administered in substantially pure form, or a pharmaceutically acceptable salt, ester or prodrug thereof, with PMEA, or a pharmaceutically acceptable salt, ester or prodrug thereof, optionally in a pharmaceutically acceptable carrier.

DETAILED DESCRIPTION OF THE INVENTION

As used herein, the term "isolated enantiomer" refers to a nucleoside composition that includes approximately 95% to 100%, or more preferably, over 97% of a single enantiomer of that nucleoside.

The terms "substantially pure form" or substantially free of its opposite enantiomer refers to a nucleoside composition of one enantiomer that includes no more than about 5% of the other enantiomer, more preferably no more than about 2%, and most preferably less than about 1% is present.

The synergistic combination of compounds or their pharmaceutically acceptable esters or salts, are also useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These synergistic formulations can also be used prophylactically to prevent or retard the progression of clinical illness in individuals who are anti-HBV antibody or HBV antigen positive or who have been exposed to HBV.

The active compound can be converted into a pharmaceutically acceptable ester by reaction with an appropriate esterifying agents, for example, an acid halide or anhydride. The compound or its pharmaceutically acceptable derivative can be converted into a pharmaceutically acceptable salt thereof in a conventional manner, for example, by treatment with an appropriate base. The ester or salt of the compound can be converted into the parent compound, for example, by hydrolysis.

The term "synergistic combination" refers to a combination of drugs which produces a synergistic effect in vivo, or alternatively in vitro as measured according to the methods described herein.

I. Active Compounds, and Physiological Acceptable Salts Thereof

The active compounds disclosed herein are therapeutic nucleosides or cyclic or acyclic nucleoside analogs with known activity against hepatitis B. It has been discovered that certain combinations of nucleosides provide an advantage over monotherapy, or over other combinations. Not all combinations of the known anti-HBV drugs provide a benefit; it is often the case that drugs act antagonistically.

The active compound can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and the 5' and $N^4$ cytosinyl or $N^6$-adeninyl acylated (esterified) derivatives of the active compound (alternatively referred to as "physiologically active derivatives"). In one embodiment, the acyl group is a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, or is a sulfonate ester such as alkyl or aralkyl sulphonyl including methanesulfonyl, phosphate, including but not limited to mono, di or triphosphate ester, trityl or monomethoxytrityl, substituted benzyl, trialkylsilyl (e.g., dimethyl-5-butylsilyl) or diphenylmethylsilyl. Aryl groups in the esters optionally comprise a phenyl group.

Modifications of the active compound, and especially at the $N^4$ cytosinyl or $N^6$ adeninyl and 5'-O positions, can affect the bioavailability and rate of metabolism of the active species, thus providing control over the delivery of the active species. Further, the modifications can affect that antiviral activity of the compound, in some cases increasing the activity over the parent compound. This can easily be assessed by preparing the derivative and testing its antiviral activity according to the methods described herein, or other methods known to those skilled in the art.

Prodrugs

Any of the anti-hepatitis B agents described herein can be administered as a prodrug to increase the activity, bioavailability, stability or otherwise alter the properties of the nucleoside. A number of hydroxyl-bound prodrug ligands are known. In general, alkylation, acylation or other lipophilic modification of the hydroxy, mono, di or triphosphate of the nucleoside will increase the stability of the nucleotide. Examples of substituent groups that can replace one or more hydrogens on the hydroxyl or phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides to achieve a desired effect.

Nonlimiting examples of U.S. patents that disclose suitable lipophilic substituents that can be covalently incorporated into the nucleoside, preferably at the 5'-OH of the nucleoside or hydroxyl of the acyclic nucleoside analogs (such as PMEA or Penciclovir), include U.S. Pat. Nos. 5,149,794 (Sep. 22, 1992, Yatvin, et al.); U.S. Pat. No. 5,194,654 (Mar. 16, 1993, Hostetler, et al.); U.S. Pat. No. 5,223,263 (Jun. 29, 1993, Hostetler, et al.); U.S. Pat. No. 5,256,641 (Oct. 26, 1993, Yatvin, et al.); U.S. Pat. No. 5,411,947 (May 2, 1995, Hostetler, et al.); U.S. Pat. No. 5,463,092 (Oct. 31, 1995, Hostetler, et al.); U.S. Pat. No. 5,543,389 (Aug. 6, 1996, Yatvin, et al.); U.S. Pat. No. 5,543,390 (Aug. 6, 1996, Yatvin, et al.); U.S. Pat. No. 5,543,391 (Aug. 6, 1996, Yatvin, et al.); and U.S. Pat. No. 5,554,728 (Sep. 10, 1996, Basava, et al.), all of which are incorporated herein by reference.

Foreign patent applications that disclose lipophilic substituents that can be attached to the active compounds of the present invention, or lipophilic preparations, include WO 89/02733, WO 90/00555, WO 91/16920, WO 91/18914, WO 93/00910, WO 94/26273, WO/15132, EP 0 350 287, EP 93917054.4, and WO 91/19721.

II. Preparation of the Active Compounds

The therapeutic nucleosides used in the synergistic compositions of the present invention and processes for preparing them are known in the art.

β-2-Hydroxymethyl-5-(5-fluorocytosin-1-yl)-1,3-oxathiolane (FTC), and its enantiomers, can be prepared by the methods disclosed in U.S. Pat. Nos. 5,204,466, 5,700,937, 5,728,575 and 5,827,727, all of which are incorporated by reference.

2'-Fluoro-5-methyl-β-L-arabinofuranolyluridine (L-FMAU) can be prepared by the methods disclosed in U.S. Pat. Nos. 5,565,438, 5,567,688 and 5,587,362 to Chu, et al. All of these patents are incorporated by reference.

Methods for the preparation of the DAPD compounds, including (2R,4R)-2-amino-9-[(2-hydroxymethyl)-1,3-dioxolan-4-yl]purine (DAPD) are disclosed in U.S. Pat. Nos. 5,767,122; 5,684,010; 5,444,063, and 5,179,104, all of which are incorporated by reference.

Penciclovir can be prepared by the methods disclosed in U.S. Pat. Nos. 5,075,445 and 5,684,153.

PMEA can be prepared by the methods disclosed in U.S. Pat. Nos. 5,641,763 and 5,142,051.

Mono, di, and triphosphate derivatives of the active nucleosides can be prepared as described according to published methods. The monophosphate can be prepared according to the procedure of Imai, et al., *J. Org. Chem.*, 34(6), 1547–1550 (June 1969). The diphosphate can be prepared according to the procedure of Davisson, et al., *J. Org. Chem.*, 52(9), 1794–1801 (1987). The triphosphate can be prepared according to the procedure of Hoard, et al., *J. Am. Chem. Soc.*, 87(8), 1785–1788 (1965).

III. Combination Therapy

It has been recognized that drug-resistant variants of HBV can emerge after prolonged treatment with an antiviral agent. Drug resistance most typically occurs by mutation of a gene that encodes for an enzyme used in the viral lifecycle, and most typically in the case of HBV, DNA polymerase. Recently, it has been demonstrated that the efficacy of a drug against HBV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination therapy. In general, combination therapy induces multiple simultaneous stresses on the virus.

EXAMPLE 1

| | |
|---|---|
| Test compounds: | DAPD, DXG, (-)-β-FTC, L-FMAU |
| DMVI assay controls: | Untreated cells, 3TC (lamivudine), penciclovir (PCV) |

Details of the assay methodology can be found in: Korba and Gerin, Antiviral Res. 19: 55–70 (1992) and Korba, Antiviral Res. 29: 49–52 (1996). The antiviral evaluations were performed on six separate cultures per each of four test concentrations. All wells, in all plates, were seeded at the same density and at the same time.

Due to the inherent variations in the levels of both intracellular and extracellular HBV DNA, only depressions greater than 3.0-fold for HBV virion DNA from the average levels for these HBV DNA forms in untreated cells are generally considered to be statistically significant [$P<0.05$] (Korba and Gerin, Antiviral Res. 19: 55–70, 1992). Typical values for extracellular HBV virion DNA in untreated cells range from 80 to 150 pg/ml culture medium (average of approximately 92 pg/ml).

For reference, the manner in which the hybridization analyses were performed for these experiments results in an equivalence of approximately 1.0 pg of extracellular HBV DNA/ml culture medium to $3 \times 10^5$ viral particles/ml.

Toxicity analyses were performed in order to access whether any observed antiviral effects are due to a general effect on cell viability. The method used was uptake of neutral red dye, a standard and widely used assay for cell viability in a variety of virus-host systems, including HSV and HIV. Details of the procedure are provided in the toxicity table legends.

EXPERIMENTAL PARAMETERS

Test compounds were received as solid material at room temperature in good package condition. Test compounds were solubilized in 100% tissue culture grade DMSO (Sigma, Corp.) at 100 mM (DAPD, FTC, L-FMAU) or 50 mM (DXG). Daily aliquots of test compounds were made in individual tubes and stored at −20° C. On each day of treatment, daily aliquots of the test compounds were suspended into culture medium at room temperature, and immediately added to the cell cultures.

For the antiviral test analyses, confluent cultures were maintained on 96-well flat bottomed tissue culture plates. Two separate (replicate) plates were used for each drug treatment. A total of 3 cultures on each plate were treated with each of the dilutions of antiviral agents (6 cultures per dilution). Cultures were treated with 9 consecutive daily doses of the test compounds. Medium was changed daily with fresh test compounds. Only extracellular (virion) HBV DNA levels were followed.

Toxicity analysis were performed in 96-well flat bottomed tissue culture plates. Cells for the toxicity analyses were cultured and treated with test compounds with the same schedule and under identical culture conditions as used for the antiviral evaluations. Each compound was tested at 4 concentrations, each in triplicate cultures. Uptake of neutral red dye was used to determine the relative level of toxicity 24 hours following the last treatment. The absorbance of internalized dye at 510 nM ($A_{510}$) was used for the quantative analysis. Values are presented as a percentage of the average $A_{510}$ values (±standard deviations) in 9 separate cultures of untreated cells maintained on the same 96-well plate as the test compounds.

Combination treatments were conducted using the primary analysis format except that 6 serial 3-fold dilutions were used for each drug combination and a total of 8 separate cultures were used for each dilution of the combinations. Compounds were mixed at molar ratios designed to give approximately equipotent antiviral effects based on the $EC_{90}$ values. Three different molar ratios were used for each combination to allow for variability in the estimates of relative potency. These molar ratios were maintained throughout the dilution series. The corresponding monotherapies were conducted in parallel to the combination treatments using the standard primary assay format.

For reporting purposes, the SI, $EC_{50}$, $EC_{90}$, and $CC_{50}$ values reported for the combination treatments are those of the first compound listed for the combination mixture. The concentrations and SI, $EC_{50}$, $EC_{90}$, and $CC_{50}$ values of the second compound in the mixture can be calculated using the molar ratio designated for that particular mixture. Further details on the design of combination analyses as conducted for this report can be found in B E Korba (1996) *Antiviral Res.* 29:49.

Analysis of synergism, additivity, or antagonism were determined by analysis of the data using the CalcuSyn™ program (Biosoft, Inc.). This program evaluates drug interactions by use of the widely accepted method of Chou and Talalay combined with a statistically evaluation using the Monte Carlo statistical package. The data are displayed in several different formats including median-effect and dose-effects plots, isobolograms, and combination index [CI] plots with standard deviations. For the latter analysis, a CI greater than 1.0 indicates antagonism and a CI less than 1.0 indicates synergism.

For the toxicity analyses associated with the combination treatments, the experimental design was limited by either/or the toxicity of the more toxic compound in the mixture or the stock concentrations (e.g. related to the total volume of DMSO that could be added to the cultures without inducing toxicity due to DMSO and not the test compounds).

Antiviral Evaluations

ASSAY CONTROLS: Within normal variations, levels of extracellular HBV (virion) DNA remained constant in the untreated cells over the challenge period. The positive treatment controls, 3TC (lamivudine) [((−)β,L,2',3'-dideoxy-3' thiacytidine] and penciclovir [PCV] (both purchased from Moraveck Biochemicals, La Brea, Calif.), induced significant depressions of HBV DNA replication at the concentrations used. The activities observed for 3TC in these analyses were consistent with previous experiments where approximately 0.15 to 0.2 μM 3TC induced a 90% depression of HBV virion DNA relative to average levels in untreated cells after 9 days of continuous treatment of 2.2.15 cells [$EC_{90}$] (for example, see Korba and Boyd, Antimicrob. Agents Chemother. (1996) 40:1282–1284). The activities observed for PCV in these analyses were higher than previously reported ($EC_{90}$ of approximately 0.7 to 0.9 uM, Korba and Boyd, Antimicrob. Agents Chemother. (1996) 40:1282–1284). However, the preparation of PCV used for these experiments has consistently produced anti-HBV activities in the range reported here in several other independent experiments.

TEST COMPOUNDS: Test compound DAPD, FTC, DXG, and L-FMAU induced significant and selective depressions in extracellular (virion) HBV DNA levels produced by 2.2.15 cells.

The antiviral activity of DAPD was enhanced by co-treatment with FTC. The antiviral activity of DAPD was synergistic at a 3:1 or a 1:1 molar ratio at all but the highest concentrations tested. As the relative concentration of FTC increased, the co-operative effects of the two agents decreased. At the 1:3 molar ratio, the two agents appeared to be antagonistic.

DAPD and PCV appeared to be antagonistic at all three molar ratios and at all concentrations.

At the 1:10 and 1:1 molar ratios, DAPD and L-FMAU appeared to be antagonistic. At the 1:3 molar ratio (approximately equipotent potencies based on the $EC_{90}$'s) the interactions of the two agents were more complex. DAPD and L-FMAU exhibited moderately synergistic to additive interactions at lower concentrations which progressed to increasingly more antagonistic interactions at higher concentrations. Subsequent testing, however, indicated that DAPD is synergistic with L-FMAU.

The antiviral activity of L-FMAU was enhanced by co-treatment with FTC. The antiviral activity of DAPD and FTC was moderately synergistic at a 3:1 or a 10:1 molar ratio at all but the highest concentrations tested. As the relative concentration of FTC increased, the cooperative effects of the two agents decreased. At the 1:1 molar ratio, the two agents appeared to be antagonistic.

The antiviral activity of L-FMAU was also enhanced by co-treatment with PCV. The antiviral activity of DAPD and PCV was weakly synergistic at a 1:1 or a 1:3 molar ratio at all concentrations tested. As the relative concentration of PCV increased, the co-operative effects of the two agents decreased. At the 1:10 molar ratio, the two agents appeared to be antagonistic.

Toxicity Evaluations

No significant toxicity (greater than 50% depression of the dye uptake levels observed in untreated cells) was observed for 3TC, PCV, or any of the test compounds at the concentrations used for the antiviral evaluations.

None of the combination treatments appeared to enhance the toxicity profiles of either agent in the different mixtures. The toxicity profiles of some of the combination mixtures was apparently higher than the corresponding monotherapies since the values are reported as a factor of the concentration of the first compound listed for each mixture. This is especially notable for the mixtures containing PCV. However, recalculation of the toxicity profiles on the basis of the second compound (e.g. PCV) in the mixtures revealed that all of the apparent toxicities were due to the more toxic compound and that no enhanced toxicity was present in these combinations.

EXAMPLE 2

| Test compounds provided: | (−)-β-FTC |
| --- | --- |
| DMVI assay controls: | untreated cells, 3TC (lamivudine), penciclovir (PCV) |

Details of the assay methodology were as given above. Test compounds were received as solid material at room temperature in good package condition. Test compounds were solubilized in 100% tissue culture grade DMSO (Sigma, Corp.) at 100 mM. Daily aliquots of test compounds were made in individual tubes and stored at −20° C.

TEST COMPOUNDS: Test compound FTC induced significant and selective depressions in extracellular (virion) HBV DNA levels produced by 2.2.15 cells.

The antiviral activity of FTC was enhanced by co-treatment with PCV. The antiviral activity of the combination therapy was synergistic at all molar ratios tested. As the relative concentration of PCV increased, the cooperative effects of the two agents decreased.

Toxicity Evaluations

No significant toxicity (greater than 50% depression of the dye uptake levels observed in untreated cells) was observed for 3TC, PCV, FTC, or any of the combination treatments at the concentrations used for the antiviral evaluations (Tables S1, T1).

None of the combination treatments appeared to enhance the toxicity profiles of either agent in the different mixtures. The toxicity profiles of some of the combination mixtures was apparently higher than the corresponding monotherapies since the values are reported as a factor of the concentration of the first compound listed for each mixture.

EXAMPLE 3

Combination Therapy with PMEA

| Test compounds provided: | PMEA, (−)-β-FTC, DAPD, L-FMAU |
| --- | --- |
| DMVI assay controls: | Untreated cells, 3TC (lamivudine) |

Details of the assay methodology were as given above. Test compounds (except for bis-POM-PMEA) were received as powdered material on dry ice in good package condition and stored at −20° C. Test compound bis-POM-PMEA was received as a 100 mM solution in DMSO. Daily aliquots of test compounds were made in individual tubes and stored at −20° C. On each day of treatment, daily aliquots of the test compounds were suspended into culture medium at room temperature, and immediately added to the cell cultures.

TEST COMPOUNDS (PRIMARY ANALYSES): All of the test compounds induced significant and selective depressions in extracellular (virion) HBV DNA levels produced by 2.215 cells. However, the potencies of test compounds (−)-β-FTC, DAPD and L-FMAU were lower than that observed in earlier analyses. This was most apparent for DAPD and L-FMAU.

Bis-POM-PMEA (BP-PMEA)+FTC. The mixture of BP-PMEA and FTC produced an anti-HBV activity that was moderately synergistic overall. The potency of the mixtures increased as the relative proportion of FTC increased. However, the most favorable overall interactions occurred where the concentration of FTC was proportionately lower. The same relative degree of synergism was generally observed at all concentrations of the 30:1 mixture. Relatively more synergistic interactions were observed at the lower concentrations of the 10:1 and 3:1 mixture and moderate to strong antagonism was observed at the highest concentrations of the 3:1 mixture.

BP-PMEA+DAPD. The mixture of BP-PMEA and DAPD produced an anti-HBV activity that was moderately to weakly synergistic at lower relative concentrations of DAPD and moderately to strongly antagonistic at higher relative concentrations of DAPD. The potency of the mixtures also decreased as the relative proportion of DAPD increased. Relatively more synergistic interactions were observe at the lower concentrations of the different mixtures.

BP-PMEA+L-FMAU. The mixture of BP-PMEA and L-FMAU produced an anti-HBV activity that was moderately synergistic at lower relative concentrations of L-FMAU and additive to weakly antagonistic at higher relative concentrations of L-FMAU. The potency of the mixtures was lowest at the highest relative concentration L-FMAU (1:1 molar ratio). The most favorable overall interactions were observed at the 3:1 molar ratio of the two compounds. Relatively more synergistic interactions were observed at the lower concentrations of different mixtures.

Toxicity Evaluations

No significant toxicity (greater than 50% depression of the dye uptake levels observed in untreated cells) was observed for 3TC, any of the test compounds, or any of the compound mixtures at the concentrations used for the antiviral evaluations. None of the compound mixtures appeared to significantly enhance toxicity. The patterns of toxicity observed for the compound mixtures was similar to, and consistent with, that observed for the monotherapies.

IV. Preparation of Pharmaceutical Compositions

Humans suffering from any of the diseases described herein arising out of HBV infection, can be treated by administering to the patient an effective amount of identified synergistic anti-HBV agents in a combination or independent dosage form for combination or alternation therapy, optionally in a pharmaceutically acceptable carrier or diluent. The active materials can be administered by any appropriate route, for example, orally, parenterally, intravenously, intradermally, subcutaneously, or topically, in liquid or solid form.

The active compounds are included in the pharmaceutically acceptable carriers or diluents in amounts sufficient to deliver to a patient a therapeutically effective amount of compound to inhibit viral replication in vivo, especially HBV replication, without causing serious toxic effects in the patient treated. By "inhibitory amount" is meant an amount of active ingredient sufficient to exert an inhibitory effect as measured by, for example, an assay such as the ones described herein.

A preferred dose of the compound for all the above-mentioned conditions will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art.

The compound is conveniently administered in unit or any suitable dosage form, including but not limited to one containing 7 to 3000 mg, preferably 70 to 1400 mg of active ingredient per unit dosage form. An oral dosage of 50–1000 mg is usually convenient, more typically 50–300 mg.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable derivative or salt thereof can also be mixed with other active materials that do not impair the desired action, or with materials that supplement the desired action, such as antibiotics, antifungals, antiinflammatories, protease inhibitors, or other nucleoside or nonnucleoside antiviral agents, as discussed in more detail above. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; cheating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triiphosphate derivatives is then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention. It is intended that all of these variations and modifications be included within the scope of this invention.

We claim:

1. A method for the treatment of hepatitis B virus in a human comprising administering in combination or alternation a synergistically effective amount of β-2-hydroxymethyl-5-(5-fluorocytosin-1-yl)-1,3-oxathiolane (β-FTC) or a pharmaceutically acceptable salt, ester, or prodrug thereof with an effective amount of penciclovir.

2. The method of claim 1, wherein the β-FTC is in the form of the (−)-optical isomer ((−)-β-FTC).

3. The method of claim 2 wherein the (−)-β-FTC is in substantially pure form including no more than about 5% of the (+)-enantiomer.

4. The method of claim 2 wherein the (−)-β-FTC is in substantially pure form including no more than about 1% of the (+)-enantiomer.

5. The method of claim 2 wherein the (−)-β-FTC is present in a nucleoside composition comprising approximately 95% to 100% of (−)-β-FTC.

6. The method of claim 2 wherein the (−)-β-FTC is present in a nucleoside composition comprising greater than 97% of (−)-β-FTC.

7. The method of claim 2 wherein the (−)-β-FTC and penciclovir are administered as oral tablets.

8. The method of claim 2 wherein the (−)-β-FTC and penciclovir are administered in combination.

9. The method of claim 2 wherein the (−)-β-FTC and penciclovir are administered in alternation.

10. The method of claim 2 wherein (−)-β-FTC is administered.

11. The method of claim 2 wherein a pharmaceutically acceptable salt of (−)-β-FTC is administered.

12. The method of claim 10 wherein the (−)-β-FTC is in substantially pure form including no more than about 5% of the (+)-enantiomer.

13. The method of claim 10 wherein the (−)-β-FTC is in substantially pure form including no more than about 1% of the (+)-enantiomer.

14. The method of claim 11 wherein the pharmaceutically acceptable salt of (−)-β-FTC is in substantially pure form including no more than about 5% of the (+)-enantiomer.

15. The method of claim 11 wherein the pharmaceutically acceptable salt of (−)-β-FTC is in substantially pure form including no more than about 1% of the (+)-enantiomer.

16. The method of claim 10 wherein the (−)-β-FTC is present in a nucleoside composition comprising approximately 95% to 100% of (−)-β-FTC.

17. The method of claim 10 wherein the (−)-β-FTC is present in a nucleoside composition comprising greater than 97% of (−)-β-FTC.

18. The method of claim 11 wherein the pharmaceutically acceptable salt of (−)-β-FTC is present in a nucleoside composition comprising approximately 95% to 100% of the pharmaceutically acceptable salt of (−)-β-FTC.

19. The method of claim 11 wherein the pharmaceutically acceptable salt of (−)-β-FTC is present in a nucleoside composition comprising greater than 97% of the pharmaceutically acceptable salt of (−)-β-FTC.

* * * * *